United States Patent [19]

Dexter et al.

[11] 4,278,590

[45] Jul. 14, 1981

[54] 2-[2-HYDROXY-3,5-DI-TERT-OCTYL-PHENYL]-2H-BENZOTRIAZOLE AND STABILIZED COMPOSITIONS

[75] Inventors: Martin Dexter, Briar Cliff Manor; Roland A. E. Winter, Armonk, both of N.Y.

[73] Assignee: Ciba-Geigy Corporation, Ardsley, N.Y.

[21] Appl. No.: 100,400

[22] Filed: Dec. 17, 1979

Related U.S. Application Data

[63] Continuation-in-part of Ser. No. 68,275, Aug. 20, 1979, which is a continuation of Ser. No. 6,391, Jan. 25, 1979, abandoned.

[51] Int. Cl.$^3$ .................................................. C08K 5/34
[52] U.S. Cl. ....................... 260/45.8 NT; 260/45.8 N; 548/260
[58] Field of Search ................ 548/260; 260/45.8 NT, 260/45.8 N

[56] References Cited

U.S. PATENT DOCUMENTS 4,041,044   8/1977   White .................................. 548/260

FOREIGN PATENT DOCUMENTS 2364947   4/1978   France .

Primary Examiner—Paul M. Coughlan, Jr.
Attorney, Agent, or Firm—Luther A. R. Hall

[57] ABSTRACT

2-[2-Hydroxy-3,5-di-tert-octylphenyl]-2H-benzotriazole exhibits outstanding efficacy in protecting organic substrates from light induced deterioration as well as good resistance to loss by volatilization or exudation during the high temperature processing of stabilized compositions.

The combination of the benzotriazole UV absorber with a hindered amine light stabilizer is particularly efficacious in protecting thermoset and thermoplastic acrylic resin automotive finishes and enamels.

13 Claims, No Drawings

2-[2-HYDROXY-3,5-DI-TERT-OCTYLPHENYL]-2H-BENZOTRIAZOLE AND STABILIZED COMPOSITIONS

This is a continuation-in-part of application Ser. No. 68,275, filed Aug. 20, 1979, which in turn is a continuation of Ser. No. 6391, filed Jan. 25, 1979, now abandoned.

BACKGROUND OF THE INVENTION

The present invention relates to selected 2-aryl-2H-benzotriazoles which are useful in protecting light-sensitive organic materials from deterioration and to stabilized compositions containing said benzotriazoles.

The UV-absorber of the o-hydroxyphenyl-2H-benzotriazole class have long been known as effective light stabilizers for organic materials and have enjoyed considerable commercial success.

The description, preparation and uses of these valuable 2-aryl-2H-benzotriazoles are further taught in U.S. Pat. Nos. 3,004,896; 3,055,896; 3,072,585; 3,074,910; 3,189,615 and 3,230,194.

However the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase compatibility and to reduce volatilization loss by modifying the structure of the benzotriazoles.

In U.S. Pat. No. 3,230,194, a higher alkyl group was substituted for methyl and the latter compound 2-(2-hydroxy-5-tert-octylphenyl)-2H-benzotriazole exhibited superior compatibility and performance in polyethylene compound to former.

Still other attempts were made to increase the compatibility of the aryl-2H-benzotriazole molecules in polymeric substrates and to decrease the tendency of said molecules to volatilize during processing and/or use by substituting the phenolic ring of said compounds with aralkyl groups such as benzyl, α-methylbenzyl and α,α-dimethylbenzyl radicals. Such compounds are disclosed in U.S. Pat. No. 4,127,586; Japanese Kokai No. 158588/75 and copending U.S. patent application Ser. No. 918,984.

Surprisingly, the instant compounds such as 2-(2-hydroxy-3,5-di-tert-octylphenyl)-2-H-benzotriazole having only alkyl substitution on the phenolic ring of the benzotriazole exhibit an excellent combination of compatibility with and/or solubility in numerous polymeric substrates along with superior resistance to loss from stabilized compositions during high temperature processing or in end use applications where coatings or films of the stabilized compositions are exposed even to ambient weathering and light exposures compared to stabilized compositions containing the closest 2-aryl-2H-benzotriazoles of the prior art.

In U.S. Pat. No. 4,041,044, an improved process for making 2-aryl-2H-benzotriazoles is taught. In said Specification, a number of phenols and some twelve preferred phenols useful in said process are listed, inter alia 2,4-di-tert-octylphenol. Neither instant compound 2-(2-hydroxy-3,5-di-tert-octylphenyl)-2H-benzotriazole nor 5-chloro-2-(2-hydroxy-3,5-di-tert-octylphenyl)-2H-benzotriazole was exemplified nor prepared in said reference and the outstanding properties of these compounds now seen compared to other prior art benzotriazoles were not then recognized from among the myriad of possible compounds disclosed in this reference.

A dyeable stabilized polymer blend comprising polypropylene, a polyetherester, two phenolic antioxidants, a thiosynergist and 2-(2-hydroxy-3,5-dioctylphenyl)-2,1,3-benzotriazole is disclosed in U.S. Pat. No. 3,487,453. The exact chemical structure of the "dioctyl" substitution on the aryl-2H-benzotriazole moiety is not further identified nor can what influence or effect the benzotriazole exerted in this complex mixture of stabilizers in polypropylene be discerned.

In copending U.S. application Ser. No. 971,271 the use of hindered amine light stabilizers to protect metallic lacquers is described.

DETAILED DISCLOSURE

This invention pertains to selected 2-aryl-2H-benzotriazole light absorbers and to organic materials, both polymeric and non-polymeric, stabilized thereby.

More particularly, the 2-aryl-2H-benzotriazoles of this invention are represented by the Formula I

[Structure: benzotriazole with $R_1$ substituent, connected via N=N to phenol ring with OH and two $R_2$ substituents] (I)

wherein
$R_1$ is hydrogen or chloro, and
$R_2$ is tert-octyl.
Preferably, $R_1$ is hydrogen.

The preferred compound is 2-[2-hydroxy-3,5-di-tert-octylphenyl]-2H-benzotriazole.

SYNTHESIS OF COMPOUNDS

The compounds of this invention are made by the following procedure:

Step I:

[Reaction: compound II with $R_1$ and $NH_2$, $NO_2$ substituents, via diazotization acid / sodium nitrite, gives compound III with $N_2^{\oplus}X^{\ominus}$ and $NO_2$ substituents]

II    III

X is an anion such as chloride or sulfate.

[Reaction: III + compound IV (phenol with OH, $R_2$, $R_2$), via coupling acid or alkaline medium, gives compound V with benzene-$NO_2$ linked via N=N to phenol with OH and two $R_2$]

IV    V

Step II:

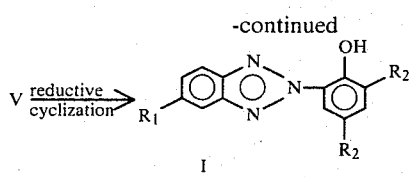

$R_1$ and $R_2$ are as described earlier in the specification.

Step I is the coupling of a diazonium compound with a phenol and can be carried out under either acid or alkaline conditions. Preferably the coupling is carried out under acid conditions to give yields of coupled product, the o-nitroazobenzene intermediate (V) in the range of over 70% of theory.

Step II involves the reductive cyclization of the intermediate V to the corresponding 2-aryl-2H-benzotriazole. This can be conveniently carried out by a number of known reduction methods including zinc and alkali, hydrazine, and catalytic hydrogenation with noble metal or nickel catalysts for this reaction. Good yields of the 2-aryl-2H-benzotriazoles are obtained by using such systems.

The various starting materials, i.e., 2,4-di-tert-octylphenol, o-nitroaniline and 5-chloro-2-nitroaniline, are largely available as items of commerce or can easily be prepared by known methods.

The compounds of this invention are effective light stabilizers in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid. 4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile. The instant compounds are advantageously used in heat-curable acrylic resin lacquers which are composed of a copolymer of acrylic acid and one or more of its derivatives, and a melamine-formaldehyde resin.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenyleneisophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and malamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

While compounds of this invention are very effective stabilizers for a host of organic substrates subject to light induced deterioration, as are the 2-aryl-2H-benzotriazole light absorbers in general, the instant compounds with their surprising resistance to loss from a stabilized composition during high temperature processing due to volatilization, exudation or sublimation have particular value in stabilizing polymeric substrated which are perforce processed at elevated temperatures.

Thus, the compounds of this invention are particularly useful as stabilizers for the protection of polyesters, for instance poly(ethylene terephthalate), poly(butylene terephthalate) or copolymers thereof; of polycarbonates, for example polycarbonate derived from bisphenol A and phosgene, or copolymers thereof; of polysulfones; of polyamides such as nylon-6, nylon-6,6, nylon 6,10 and the like as well as copolyamides; of thermoset acrylic resins; of thermoplastic acrylic resins; of polyolefins such as polyethylene, polypropylene, copolyolefins and the like; and of any polymer system requiring high temperature processing and fabrication.

Certain hydrophobic nondiffusing hydroxyphenylbenzotriazoles are disclosed as very useful as ultraviolet light absorbers in photographic gelatin layers (U.S. Pat. No. 3,253,921). The instant benzotriazoles with their great resistance to volatilization, their enhanced solubility in selected solvents, their desirable absorption characteristics in the ultraviolet range and their photographic inertness are particularly useful in photographic compositions, especially in protecting color dye images against the harmful effects of ultraviolet light.

Of particular interest are the thermoplastic acrylic resins and the thermoset acrylic resins used in automatic finishes and enamels. These materials are described in the Encyclopedia of Polymer Science and Technology, Interscience Publishers, New York, Vol 1 (1964), pages 273–276, and Vol 13 (1970), pages 530–532; and W. R. Fuller, "Understanding Paint," American Paint Journal Co., St. Louis, 1965, pages 124–135.

The acrylic resin lacquers which according to the invention can be stabilised against light, moisture and oxygen are the customary acrylic resin stoving lacquers, such as are described for example in H. Kittel's 'Lehrbuch der Lacke und Beschichtungen' (Textbook of Lacquers and Coatings), Volume 1, part 2 on pages 735 and 742 (Berlin, 1972), and in H. Wagner, H. F. Sarx, 'Lackkunstharze' (Synthetic resins for Lacquers), on pages 229–235.

Of particular interest is the stabilisation, according to the invention, of metallic lacquers based on hot-cross-linkable polyacrylate resins which contain styrene incorporated by polymerisation. It would be possible with these resins to produce metallic lacquers having excellent physical and chemical properties if it were not for the formation of cracking on weathering, depending of the content of incorporated styrene. Other lacquers and enamels are those based on alkyl-melamine and alkyd-acrylic malamine resins.

For obtaining the metallic effect, there are used the aluminium pigments normally employed for this purpose in an amount of 1 to 10 percent by weight, relative to the solvent-free binder (lacquer resin). The application of the metallic lacquers stabilised according to the invention is effected preferably, in the usual manner, by one of two processes; either by the single-layer process or by the two-layer process. In the latter case, the layer containing the aluminium pigment is firstly applied, and then over this is applied a covering clear-lacquer layer.

The instant compounds also provide excellent dye light stability to dyed polyamide and polyaramid fibers, such as nylon-6-6, nylon 6, poly(m-phenylene isophthalamide) fibers.

Four outstanding properties distinguish the instant compounds over the very close benzotriazoles of the prior art. These are:
  1. lower volatility
  2. greater solubility in common organic solvents used in polymer coating operations
  3. greater compatibility in polyolefins, polyhydrocarbons, and other vinyl polymers
  4. resistance to discoloration in the presence of some metal ions encountered in many polymer stabilizer or curing systems.

The practical and economic advantages flowing from each of these really unexpectedly better properties of the instant compounds compared to the prior are benzotriazoles are as follows:

a. Lower volatility, especially when combined with good polymer compatibility and/or solvent solubility, permits the instant benzotriazole compound to be incorporated into a polymer, to remain there even after high temperature processing, and to provide the ultimate fabricated product with desired light stabilization protection. If a stabilizer, no matter how effective it may be, is lost during processing, it cannot provide light protection to the fabricated product.

b. As can be seen in the table below, the instant compound of Example 1, 2-(2-hydroxy-3,5-di-tert-octylphenyl)-2H-benzotriazole is appreciably more soluble in common organic solvents used in coating operations than close prior art compound TINUVIN 328, 2-(2-hydroxy-3,5-di-tert-amylphenyl)-2H-benzotriazole.

| Solvent | Solubility Grams/100 ml solvent at 20° C. | |
|---|---|---|
| | Compound 1 (Example 2) | TINUVIN 328 |
| xylene | 56 | 44 |
| hexane | 35 | 16 |
| ethyl acetate | 35 | 16 |
| styrene | 67 | 40 |

The increased solubility of the instant compounds permits the preparation of more concentrated solids solutions of the instant compounds, reduces the volume of organic solvents to be handled (a major concern in environmental protection considerations as well as for economic reasons) and permits the practical use of less toxic solvents such as hexane in place of aromatic solvents.

c. Greater compatibility of the instant compounds in the polymeric substrates, coupled with reduced volatility discussed above, permits high temperature processing and high temperature use of stabilized products as well as extended ambient temperature use of said products. The undersirable exudation of a stabilizer onto processing equipment (causing frequent and costly premature equipment shutdowns) is prevented as well as exudation of the stabilizer (blushing) during use of the fabricated fiber or polymer. Such exudation is unsightly aesthetically, is costly in the premature loss of stabilizer and in the shortened product life of the fiber or polymer product from which the exuded stabilizer has escaped without exerting its desired function.

d. Surprisingly, the instant compounds exhibit resistance to discoloration with various metal ions encountered in many polymer stabilizer on curing systems. Many prior art benzotriazole compounds apparently form colored complexes of indeterminate structure with metal ions such as cobalt, iron, barium, cadimuim, tin and the like.

Polymer systems, such as unsaturated polyesters, alkyds, and the like wherein metal salts such as cobalt napthenate are used as dryers; poly(vinyl chloride) (PVC) or PVC copolymers stabilized with barium-cadmium or tin compounds; polyurethane systems containing tin catalysts; ABS resins containing iron impurities; represent substrates in which the instant benzotriazoles would have beneficial properties due to the apparent absence of complex formation between the instant benzotriazoles and said metal ions.

This is demonstrated by the Gardner color numbers for a xylene solution of various benzotriazole compounds before and after the addition of two drops of a 6% cobalt naphthenate solution (in xylene).

| | Resistance to Discoloration | |
|---|---|---|
| | Gardner Color Number** | |
| Stabilizer* | Before | After adding Cobalt naphthenate |
| None | — | purplish color |
| Compound 1 (Example 2) | 1 | slight purplish color |
| TINUVIN 328 | 1 | 3.5 |
| TINUVIN P | 1 | 10 |
| UV 5411 | 1 | 10 |

*TINUVIN 328 = 2-(2-hydroxy-3,5-di-tert-amylphenyl)-2H-benzotriazole.
TINUVIN P = 2-(2-hydroxy-5-methylphenyl)-2H-benzotriazole.
UV 5411 = 2-(2-hydroxy-5-tert-octylphenyl)-2H-benzotriazole.
**Gardner color number 1 is colorless (no yellow); 3.5 is perceptibly yellow; 10 (very yellow).

The discoloration caused by the apparent complexing of some benzotriazoles with various metal ions is often alone a sufficiently serious disadvantage to prevent the use of such benzotriazoles in any systems containing the metal ions. In other cases where the level of discoloration might be tolerated itself, the complex formation itself is disadvantageous by preventing the dryer from exercising its curing effects or the stabilizer from providing stabilization. In these cases, clearly the use of the prior art benzotriazoles would be counterindicated.

e. Finally in some thermoset acrylic resin systems crosslinked by melamine curing systems, curing is sometimes retarded by the presence of some prior art benzotriazoles. It is now seen that the instant benzotriazoles, presumedly due to some unexpected structural configuration around the hydroxyl group, do not interact with melamine curing agents in thermoset acrylic resin systems in contrast to some prior art benzotriazoles.

This is confirmed by compariing the pendulum hardness values of a thermoset acrylic resin film cured in the absence of any light stabilizer with the same resin films cured in the presence of 1% of a benzotriazole light stabilizer.

| | Thermoset Acrylic Resin Film* Pendulum Hardness Values |
|---|---|
| Stabilizer | Pendulum Hardness Value** After Curing (25 minutes at 140° C.) |
| None | 123 |
| TINUVIN 328 (1%)*** | 90 |
| Compound 1(1%) (Example 2) | 126 |

*Resin is a styrene substituted acrylic copolymer cross-linked with an alkylated melamine curing system.
**The higher the number, the harder the coating.
***TINUVIN 328 is 2-(2-hydroxy-3,5-di-tert-amylphenyl)-2H-benzotriazole.

While the phenomenon is not understood, the instant benzotriazoles surprisingly do not retard or interfere with the curing of thermoset acrylic resin systems as witnessed by the retention or even enhancing of pendulum hardness values which are a direct measure of the amount and completeness of resin curing as sharply contrasted with a benzotriazole of the prior art having a closely related structure.

Although the compounds of the invention may be used above to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.1 to about 5% by weight of the stabilized composition, although this will vary with the particular substrate and application. An advantageous range is from about 0.3 to about 3%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.1 to about 5%, preferably from about 0.3 to about 3% by weight of various conventional additives, such as the following, particularly phenolic antioxidants or light-stabilizers, or mixtures thereof:

1. Antioxidants
1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.
1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.
1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.
1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)pentane and ethylene glycol bis-[3,3-bis-(3-tert.-butyl-4-hydroxyphenyl)-butyrate].
1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example 2,4-bis-octylmercapto-6-(3,5-di-tert.-butyl-4-hydroxy-anilino)-s-triazine, 2-octylmercapto-4,6-bis-(3,5-di-tert.butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexnediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methyl-phenylpropionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1.9-nonanediol, ethylene glycol, 1,2-propenediol, diethylene glycol, thio-diethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines, e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-penbis-(2,2,6,6-tetramethylpiperidyl) sebacate, bis-(1,2,2,6,6-pentamethylpiperidyl) 2-n-butyl-2-(2-hydroxy-3,5-di-tert.-butylbenzyl)malonate or 3-n-octyl-7,7,9,9-trimethyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho-and para-methoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylideneoxalic acid dihydrazide, N,N'-diacetaladipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodipropionate, lubricants such as stearyl alcohol, fillers, asbestos, kaolin, talc, glass fibers, pigments, optical brighteners, flameproofing agents and antistatic agents.

The combination of a hindered amine light stabilizer and an instant benzotriazole UV light stabilizer provides a particularly beneficial solution to the combined goal of gloss retention and delamination resistance in metallic thermoset acrylic enamels and in metallic thermoplastic acrylic lacquers for automotive topcoats.

The hindered amine light stabilizers protect the thermoset acrylic enamels and thermoplastic acrylic lacquers against loss of gloss on weathering, but do not act as UV light screens. Accordingly, UV light can pass through the acrylic topcoat in the absence of a UV light absorber and failure of the epoxy ester primer surface beneath the topcoat can then occur.

The addition of an instant benzotriazole UV light absorber into the acrylic topcoat prevents UV light from passing through and causing deterioration of the primer surface beneath.

Thus, a combination of hindered amine with benzotriazole in the acrylic topcoat provides both gloss retention and resistance to delamination for the metallic acrylic topcoats.

The hindered amine is effective in this composition in preventing gloss at the 0.1 to 5%, preferably 0.5 to 2%, and most preferably at the 0.5 to 1% by weight level based on the acrylic topcoat resin.

The instant benzotriazole is effective in preventing delamination of the acrylic topcoat at the 0.1 to 5%, preferably 0.5 to 2%, and most preferably at the 0.5 to 1% by weight level based on the acrylic topcoat resin.

The hindered amine light stabilizers useful in this invention are described by the general formula

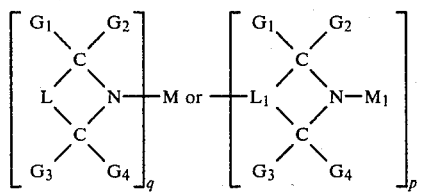

wherein q is 1 or 2, p is 2 to 14, $G_1$, $G_2$, $G_3$ and $G_4$ are independently alkyl; or $G_1$ and $G_3$ together are alkylene or each are carboalkoxy or carbophenethoxy; or $G_1$ and $G_2$ or $G_3$ and $G_4$, independently of one another, together are alkylene or azaalkylene, if q is 1, m is hydrogen, hydroxyl, oxyl, optionally substituted alkyl, alkenyl, alkynyl, aralkyl, alkanoyl, alkenoyl, benzoyl, glycidyl or —CH$_2$CHOHZ where Z is hydrogen, methyl or phenyl, if q is 2, M is alkylene, alkenylene, alkynylene, arylenedialkylene, the group —(CH$_2$)$_2$OOCR$_{1-8}$COO(CH$_2$)$_2$— or the group —CH$_2$OOCR$_{1-9}$COOCH$_2$— where $R_{18}$ is alkylene and $R_{19}$ is alkylene, xylylene or cyclohexylene, $M_1$ has the meaning of M where q is 1, L is a divalent organic radical which supplements the N-containing ring to form a 5 to 7 membered ring, or is two monovalent organic radicals, and $L_1$ is a divalent organic radical which supplements the N-containing ring to form a 5 to 7 membered ring and which additionally provides a linking group to other hindered amine moieties.

Among the hindered amines useful in this invention are compounds having the formula

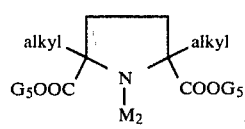

where $G_5$ is hydrogen, alkyl or phenethyl and $M_2$ is hydrogen, hydroxyl, oxyl, alkyl, 2-methoxyethyl, alkenyl or propargyl.

The hindered amine light stabilizers useful in the instant invention are in particular 2,2,6,6-tetraalkylpiperidine compounds which contain a group of the formula (I)

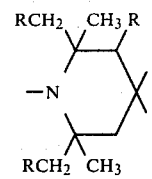

in which R is hydrogen or methyl.

The light stabilisers to be used according to the invention include in particular the following classes of compounds:

(a) Light stabilisers of the formula (II)

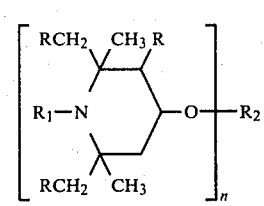

in which n is a number for 1–4 inclusive, preferably 1 or 2; R is as defined under the formula (I); $R_1$ is hydrogen, oxyl, $C_1$–$C_{18}$ alkyl, $C_3$–$C_8$ alkenyl, $C_3$–$C_8$ alkynyl, $C_7$–$C_{12}$ aralkyl, $C_1$–$C_8$ alkanoyl, $C_3$–$C_5$ alkenoyl, glycidyl, a group —CH$_2$CH(OH)—Z wherein Z is hydrogen, methyl or phenyl, with $R_1$ preferably being hydrogen, $C_1$–$C_{12}$ alkyl, allyl, benzyl, acetyl or acryloyl; and $R_2$ when n is 1 is hydrogen, $C_1$–$C_{18}$ alkyl optionally interrupted by one or more oxygen atoms, cyanoethyl, benzyl, glycidyl, a monovalent radical of an aliphatic, cycloaliphatic, araliphatic or aromatic carboxylic acid, or of carbamic acid or of a phosphorus-containing acid, or a monovalent silyl radical, preferably a radical of an aliphatic carboxylic acid having 2–18 C atoms, of a cycloaliphatic carboxylic acid having 5–12 C atoms or of an aromatic carboxylic acid having 7–15 C atoms; $R_2$ when n is 2 is $C_1$–$C_{12}$ alkylene, $C_4$–$C_{12}$ alkenylene, xylylene, a bivalent radical of an aliphatic, cycloaliphatic, araliphatic or aromatic dicarboxylic acid, of dicarbamic acid or of a phosphorus-containing acid, or a bivalent silyl radical, preferably a radical of an aliphatic dicarboxylic acid having 2–36 C atoms, of a cycloaliphatic or aromatic dicarboxylic acid having 8–14 C atoms, or of an aliphatic, cycloaliphatic or aromatic dicarbamic acid having 8–14 C atoms; $R_2$ when n is 3 is a trivalent radical of an aliphatic, cycloaliphatic or aromatic tricarboxylic acid, of an aromatic tricarbamic acid or of a phosphorus-containing acid, or a trivalent silyl radical; and $R_2$ when n is 4 is a tetravalent radical of an aliphatic, cycloaliphatic or aromatic tetracarboxylic acid.

If any substituents are $C_1$–$C_{12}$ alkyl, they are for example methyl, ethyl, n-propyl, n-butyl; sec-butyl, tert-butyl, n-hexyl, n-octyl, 2-ethyl-hexyl, n-nonyl, n-decyl, n-undecyl or n-dodecyl.

As $C_1$–$C_{18}$ alkyl, $R_1$ or $R_2$ can be for example the groups given above, and in addition for example n-tridecyl, n-tetradecyl, n-hexadecyl or n-octadecyl.

When $R_1$ is $C_3$–$C_8$ alkenyl, it can be for example 1-propenyl, allyl, methallyl, 2-butenyl, 2-pentenyl, 2-hexenyl, 2-octenyl or 4-tert-butyl-2-butenyl.

As $C_3$–$C_8$ alkynyl, $R_1$ is preferably propargyl.

$R_1$ as $C_7$–$C_{12}$ aralkyl is in particular phenethyl or especially benzyl.

As $C_1$–$C_8$ alkanoyl, $R_1$ is for example formyl, propionyl, butyryl, octanoyl but preferably acetyl, and as $C_3$–$C_5$ alkenoyl, $R_1$ is particularly acryloyl.

If $R_2$ is a monovalent radical of a carboxylic acid, it is for example a radical of acetic acid, stearic acid, salicylic acid, methacrylic acid, maleic acid, benzoic acid or β-(3,5-di-tert-butyl-4-hydroxyphenyl)-propionic acid.

If $R_2$ is a bivalent radical of a dicarboxylic acid, it is for example a radical of adipic acid, suberic acid, sebacic acid, phthalic acid, dibutylmalonic acid, dibenzylmalonic acid or butyl-(3,5-di-tert-butyl-4-hydroxybenzyl)malonic acid, or bicycloheptenedicarboxylic acid.

If $R_2$ is a trivalent radical of a tricarboxylic acid, it is for example a radical of trimellitic acid or of nitrilotriacetic acid.

If $R_2$ is a tetravalent radical of a tetracarboxylic acid, it is for example a radical of pyromellitic acid.

If $R_2$ is a bivalent radical of a dicarbamic acid, it is for example a radical of hexamethylenedicarbamic acid or of 2,4-toluylenedicarbamic acid.

The following compounds are examples of polyalkylpiperidine light stabilisers of this class:
(1) 4-hydroxy-2,2,6,6-tetramethylpiperidine,
(2) 1-allyl-4-hydroxy-2,2,6,6-tetramethylpiperidine,
(3) 1-benzyl-4-hydroxy-2,2,6,6-tetramethylpiperidine,
(4) 1-(4-tert-butyl-2-butenyl)-4-hydroxy-2,2,6,6-tetramethylpiperidine,
(5) 4-stearoyloxy-2,2,6,6-tetramethylpiperidine,
(6) 1-ethyl-4-salicyloyloxy-2,2,6,6-tetramethylpiperidine,
(7) 4-methacryloyloxy-1,2,2,6,6-pentamethylpiperidine,
(8) 1,2,2,6,6-pentamethylpiperidin-4-yl-β-(3,5-ditert-butyl-4-hydroxyphenyl)-propionate,
(9) 1-benzyl-2,2,6,6-tetramethyl-4-piperidinylmaleinate,
(10) (di-2,2,6,6-tetramethylpiperidin-4-yl)-adipate.
(11) (di-2,2,6,6-tetramethylpiperidin-4-yl)-sebacate,
(12) (di-1,2,3,6-tetramethyl-2,6-diethyl-piperidin-4-yl)-sebacate,
(13) (di-1-allyl-2,2,6,6-tetramethyl-piperidin-4-yl)-phthalate,
(14) 1-propargyl-4-β-cyanoethyloxy-2,2,6,6-tetramethylpiperidine,
(15) 1-acetyl-2,2,6,6-tetramethylpiperidin-4-yl-acetate,
(16) trimellitic acid-tri-(2,2,6,6-tetramethylpiperidin-4-yl) ester,
(17) 1-acryloyl-4-benzyloxy-2,2,6,6-tetramethylpiperidine,
(18) dibutyl-malonic acid-di-(1,2,2,6,6-pentamethylpiperidin-4-yl) ester,
(19) butyl-(3,5-di-tert-butyl-4-hydroxybenzyl)-malonic acid-di-(1,2,2,6,6-pentamethylpiperidin-4-yl) ester,
(20) dibenzyl-malonic acid-di-(1,2,2,6,6-pentamethylpiperidin-4-yl) ester,
(21) dibenzyl-malonic acid-di-(1,2,3,6-tetramethyl-2,6-diethyl-piperidin-4-yl) ester,
(22) hexane-1′,6′-bis-(4-carbamoyloxy-1-n-butyl-2,2,6,6-tetramethylpiperidine),
(23) toluene-2′,4′-bis-(4-carbamoyloxy-1-n-propyl-2,2,6,6-tetramethylpiperidine),
(24) dimethyl-bis-(2,2,6,6-tetramethylpiperidine-4-oxy)-silane,
(25) phenyl-tris-(2,2,6,6-tetramethylpiperidine-4-oxy)-silane,
(26) tris-(1-propyl-2,2,6,6-tetramethylpiperidin-4-yl) phosphite,
(27) tris-(1-propyl-2,2,6,6-tetramethylpiperidin-4-yl) phosphate, and
(28) phenyl-[bis-(1,2,2,6,6-pentamethylpiperidin-4-yl)]phosphonate.

(b) Light stabilisers of the formula (III)

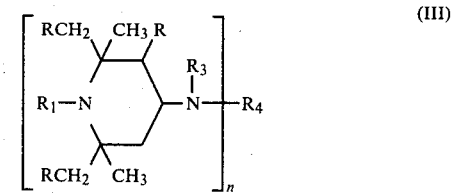

in which n is the number 1 or 2; R is as defined under the formula I; $R_1$ is as defined under (a); $R_3$ is hydrogen, $C_1$–$C_{12}$ alkyl, $C_5$–$C_7$ cycloalkyl, $C_7$–$C_8$ aralkyl, $C_2$–$C_{18}$ alkanoyl, $C_3$–$C_5$ alkenoyl or benzoyl; and $R_4$ when n is 1 is hydrogen, $C_1$–$C_{18}$ alkyl, $C_5$–$C_7$ cycloalkyl, $C_2$–$C_8$ alkenyl unsubstituted or substituted by a cyano, carbonyl or carbamide group, or it is glycidyl, a group of the formula —$CH_2$—CH(OH)—Z or of the formula —CONH—Z wherein Z is hydrogen, methyl or phenyl; or $R_4$ when n is 2 is $C_2$–$C_{12}$ alkylene, $C_6$–$C_{12}$ arylene, xylilene, a —$CH_2$—CH(OH)— $CH_2$ group, or a group —$CH_2$—CH(OH)—$CH_2$—O—X—O—$CH_2$—CH(OH)—$CH_2$— wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a bivalent radical of an aliphatic, cycloaliphatic or aromatic dicarboxylic acid or dicarbamic acid, or can be the group —CO—; or $R_3$ and $R_4$ together when n is 1 can be the cyclic radical of an aliphatic or aromatic 1,2- or 1,3-dicarboxylic acid.

If any substituents are $C_1$–$C_{18}$ alkyl, they are as already defined under (a).

If any substituents are $C_5$–$C_7$ cycloalkyl, they are in particular cyclohexane.

As $C_7$–$C_8$ aralkyl, $R_3$ is particularly phenethyl or above all benzyl.

As $C_2$–$C_{18}$ alkanoyl, $R_3$ is for example propionyl, butyryl, octanoyl, dodecanoyl, hexadecanoyl, octadecanoyl but preferably acetyl; and as $C_3$–$C_5$ alkenoyl, $R_3$ is in particular acryloyl.

If $R_4$ is $C_2$–$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$–$C_{12}$ alkylene, they are for example ethylene, propylene, 2,2-dimethylpropylene, tetramethylene, hexamethylene, octamethylene, decamethylene or dodecamethylene.

If any substituents are $C_6$–$C_{15}$ arylene, they are for example o-, m- or p-phenylene, 1,4-naphthylene or 4,4′-diphenylene.

As $C_6$–$C_{12}$ cycloalkylene, X is especially cyclohexylene.

The following compounds are examples of polyalkylpiperidine light stabilisers of this class.
(29) N,N′-bis-(2,2,6,6-tetramethylpiperidin-4-yl)hexamethylene-1,6-diamine,
(30) N,N′-bis-(2,2,6,6-tetramethylpiperidin-4-yl)hexamethylene-1,6-diacetamide,
(31) 1-acetyl-4-(N-cyclohexylacetamido)-2,2,6,6-tetramethylpiperidine,
(32) 4-benzylamino-2,2,6,6-tetramethylpiperidine,

(33) N,N'-bis-(2,2,6,6-tetramethylpiperidin-4-yl)-N,N'-dibutyl-adipamide,
(34) N,N'-bis-(2,2,6,6-tetramethylpiperidin-4-yl)-N,N'-dicyclohexyl-(2-hydroxypropylene),
(35) N,N'-bis-(2,2,6,6-tetramethylpiperidin-4-yl)-p-xylene-diamine,
(36) the compound of the formula

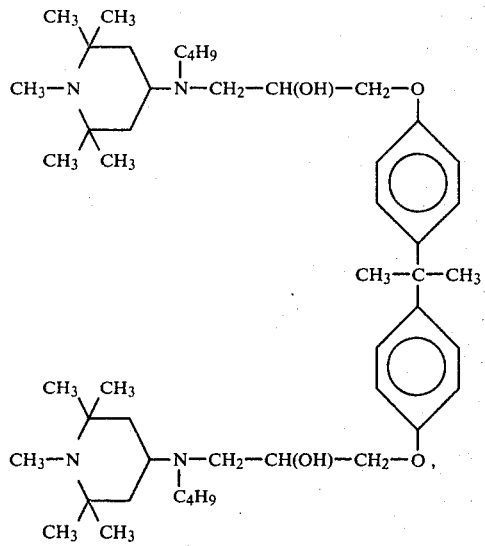

(37) 4-(bis-2-hydroxyethyl)-amino-1,2,2,6,6-pentamethylpiperidine,
(38) 4-(3-methyl-4-hydroxy-5-tert-butyl-benzoic acid-amido)-2,2,6,6-tetramethylpiperidine,
(39) 4-methacrylamido-1,2,2,6,6-pentamethylpiperidine, and
(40) α-cyano-β-methyl-β-[N-(2,2,6,6-tetramethylpiperidin-4-yl)]-amino-acrylic acid methyl ester.

(c) Light stabilisers of the formula (IV)

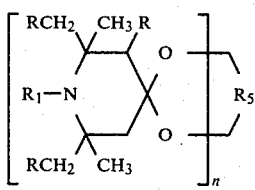

in which n is the number 1 or 2; R is as defined under the formula (I); $R_1$ is as defined under (a); and $R_5$ when n is 1 is $C_2$–$C_8$ alkylene or hydroxyalkylene or $C_4$–$C_{22}$ acyloxyalkylene; and $R_5$ when n is 2 is the group $(-CH_2)_2C(CH_2-)_2$.

If $R_5$ is $C_2$–$C_8$ alkylene or hydroxyalkylene, it is for example ethylene, 1-methyl-ethylene, propylene, 2-ethylpropylene or 2-ethyl-2-hydroxymethylpropylene.

As $C_4$–$C_{22}$ acyloxyalkylene, $R_5$ is for example 2-ethyl-2-acetoxymethyl-propylene.

The following compounds are examples of polyalkylpiperidine light stabilisers of this class:
(41) 9-aza-8,8,10,10-tetramethyl-1,5-dioxaspiro-[5.5]undecane,
(42) 9-aza-8,8,10,10-tetramethyl-3-ethyl-1,5-dioxaspiro[5.5]decane,
(43) 8-aza-2,7,7,8,9,9-hexamethyl-1,4-dioxyspiro[4.5]decane,
(44) 9-aza-3-hydroxymethyl-3-ethyl-8,8,9,10,10-pentamethyl-1,5-dioxaspiro[5.5]undecane,
(45) 9-aza-3-ethyl-3-acetoxymethyl-9-acetyl-8,8,10,10-tetramethyl-1,5-dioxaspiro[5.5]undecane, and
(46) 2,2,6,6-tetramethylpiperidine-4-spiro-2'-(1',3'-dioxane)-5'-spiro-5''-(1'',3''-dioxane)-2''-spiro-'''-(2''', 2''', 6''', 6'''-tetramethylpiperidine).

(d) Light stabilisers of the formula (V)

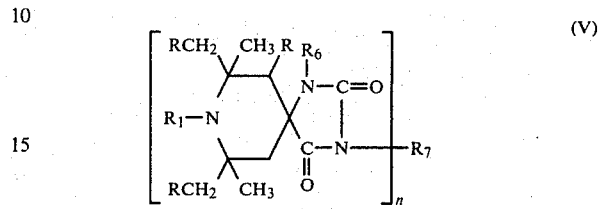

in which n is the number 1 or 2; R is as defined under the formula (I); $R_1$ is as defined under (a); $R_6$ is hydrogen, $C_1$–$C_{12}$ alkyl, allyl, benzyl, glycidyl or $C_2$–$C_6$ alkoxyalkyl; and $R_7$ when n is 1 is hydrogen, $C_1$–$C_{12}$ alkyl, $C_3$–$C_5$ alkenyl, $C_7$–$C_9$ aralkyl, $C_5$–$C_7$ cycloalkyl, $C_2$–$C_4$ hydroxyalkyl, $C_2$–$C_6$ alkoxyalkyl, $C_6$–$C_{10}$ aryl, glycidyl, a group of the formula $-(CH)-COO-Q$ or of the formula $-(CH_2)_m-O-CO-Q$ wherein m is 1 or 2, and Q is $C_1$–$C_4$ alkyl or phenyl; or $R_7$ when n is 2 is $C_2$–$C_{12}$ alkylene, $C_6$–$C_{12}$ arylene, a group $-CH_2-CH(OH)-CH_2-O-X-O-CH_2-CH(OH)-CH_2-$ wherein X is $C_2$–$C_{10}$ alkylene, $C_6$–$C_{15}$ arylene or $C_6$–$C_{12}$ cycloalkylene, or a group $-CH_2CH(OZ')CH_2-(OCH_2-CH(OZ')CH_2)_2-$ wherein Z' is hydrogen, $C_1$–$C_{18}$ alkyl, allyl, benzyl, $C_2$–$C_{12}$ alkanoyl or benzoyl.

If any substituents are $C_1$–$C_{12}$ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl or n-dodecyl.

As $C_1$–$C_{18}$ alkyl, Z' can be for example the groups stated above, and in addition for example n-tridecyl, n-tetradecyl, n-hexadecyl or n-octadecyl.

If any substituents are $C_2$–$C_6$ alkoxyalkyl, they are for example methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

If $R_7$ is $C_3$–$C_5$ alkenyl, it is for example 1-propenyl, allyl, methallyl, 2-butenyl or 2-pentenyl.

As $C_7$–$C_9$ aralkyl, $R_7$ is in particular phenethyl or above all benzyl; and as $C_5$–$C_7$ cycloalkyl, $R_7$ is especially cyclohexyl.

If $R_7$ is $C_2$–$C_4$ hydroxyalkyl, it is for example 2-hydroxyethyl, 2-hydroxypropyl, 3-hydroxypropyl, 2-hydroxybutyl or 4-hydroxybutyl.

As $C_6$–$C_{10}$ aryl, $R_7$ is in particular phenyl, or α- or β-naphthyl which is unsubstituted or substituted by halogen or $C_1$–$C_4$ alkyl.

If $R_7$ is $C_2$–$C_{12}$ alkylene, it is for example ethylene, propylene, 2,2-dimethylpropylene, tetramethylene, hexamethylene, octamethylene, decamethylene or dodecamethylene.

If $R_7$ is $C_6$–$C_{12}$ arylene, it is for example o-, m- or p-phenylene, 1,4-naphthylene or 4,4'-diphenylene.

If Z' is $C_2$–$C_{12}$ alkanoyl, it is for example propionyl, butyryl, octanoyl, dodecanoyl or preferably acetyl.

As $C_2$–$C_{10}$ alkylene, $C_6$–$C_{15}$ arylene or $C_6$–$C_{12}$ cycloalkylene, X has the meaning given under (b).

The following compounds are examples of polyalkyl-piperidine light stabilisers of this class:

(47) 3-benzyl-1,3,8-triaza-7,7,9,9-tetramethylspiro[4.5]decane-2,4-dione,
(48) 3-n-octyl-1,3,8-triaza-7,7,9,9-tetramethylspiro[4.5]decane-2,4-dione,
(49) 3-allyl-1,3,8-triaza-1,7,7,9,9-pentamethylspiro[4.5]decame-2,4-dione,
(50) 3-glycidyl-1,3,8-triaza-7,7,8,9,9-pentamethylspiro[4.5]decane-2,4-dione, or the compounds of the following formulae:

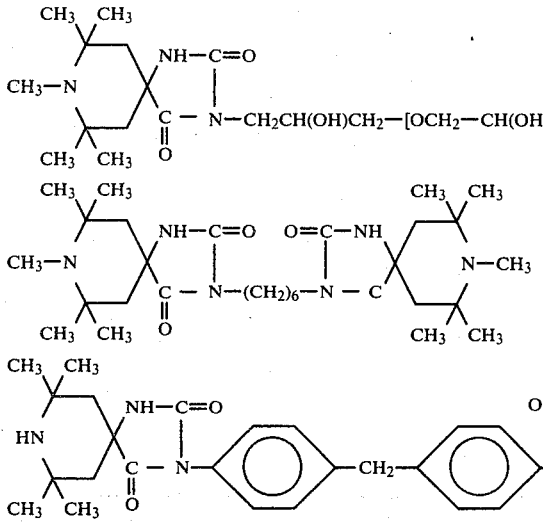

(51)

(52)

(53)

(e) Light stabilisers of the formula (VI)

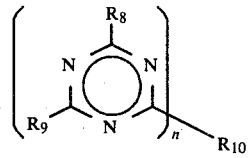

(VI)

in which n is the number 1 or 2, and $R_8$ is a group of the formula

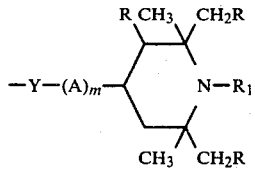

in which R is as defined under the formula (I), $R_1$ is as defined under (a), Y is —O— or —$NR_{11}$—, A is $C_2$-$C_6$ alkylene; and m is the number 0 or 1; $R_9$ is the groups $R_8$, $NR_{11}R_{12}$, —$OR_{13}$, —$NHCH_2OR_{13}$ or —$N(CH_2OR_{13})_2$; $R_{10}$ when n is 1 is the groups $R_8$ or $R_9$, and $R_{10}$ when n is 2 is the group —Y—Q—Y— wherein Q is $C_2$-$C_6$ alkylene optionally interrupted by —$N(R_{14})$—; $R_{11}$ is $C_1$-$C_{12}$ alkyl, cyclohexyl, benzyl or $C_1$-$C_4$ hydroxyalkyl, or a group of the formula

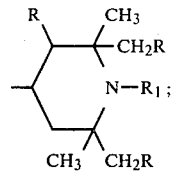

$R_{12}$ is $C_1$-$C_{12}$ alkyl, cyclohexyl, benzyl or $C_1$-$C_4$ hydroxyalkyl; $R_{13}$ is hydrogen, $C_1$-$C_{12}$ alkyl or phenyl; and $R_{14}$ is hydrogen or the group —$CH_2OR_{13}$; or $R_{11}$ and $R_{12}$ together are $C_4$-$C_5$ alkylene or oxaalkylene, or $R_{11}$ and $R_{12}$ are each a group of the formula

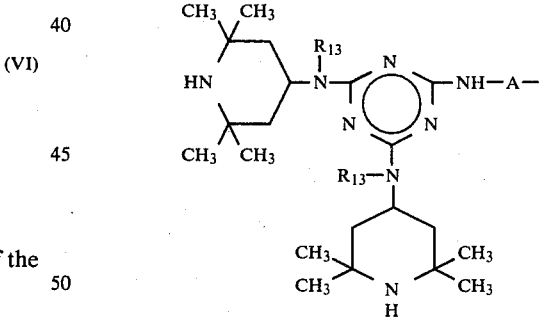

If any substituents are $C_1$-$C_{12}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl or n-dodecyl.

If any substituents are $C_1$-$C_4$ hydroxyalkyl, they are for example 2-hydroxyethyl, 2-hydroxypropyl, 3-hydroxypropyl, 2-hydroxybutyl or 4-hydroxybutyl.

If A is $C_2$-$C_6$ alkylene, it is for example ethylene, propylene, 2,2-dimethylpropylene, tetramethylene or hexamethylene.

If $R_{11}$ and $R_{12}$ together are $C_4$-$C_5$ alkylene or oxaalkylene, this is for example tetramethylene, pentamethylene or 3-oxapentamethylene.

The compounds of the following formulae are examples of polyalkylpiperidine light stabilisers of this class:

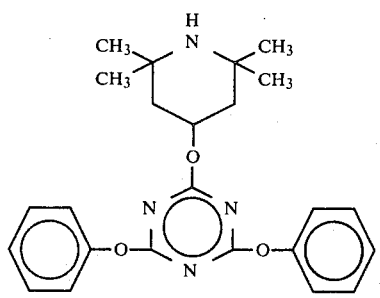
(54)
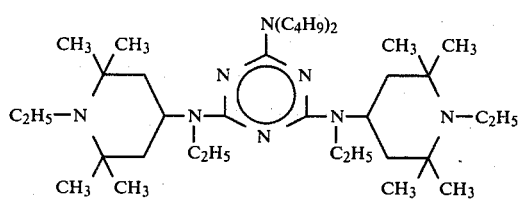
(55)
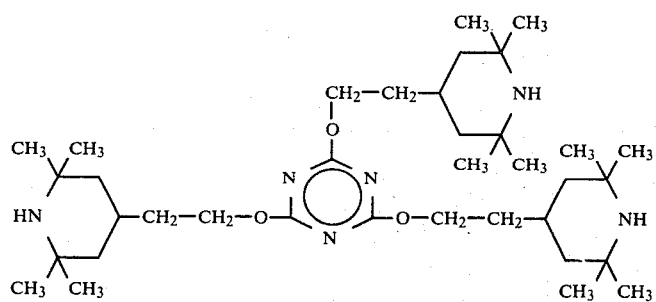
(56)
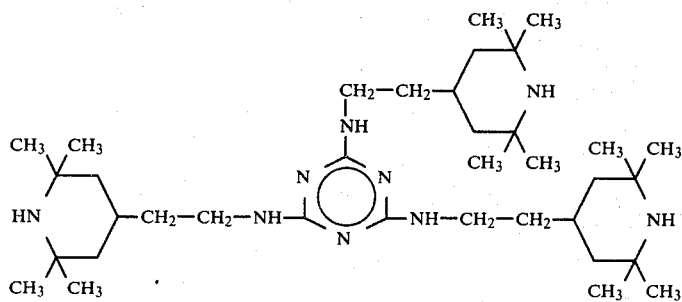
(57)
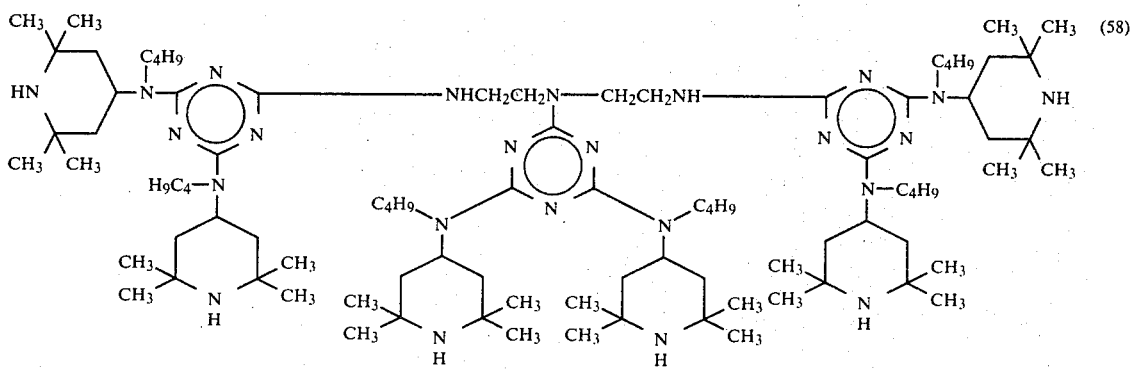
(58)

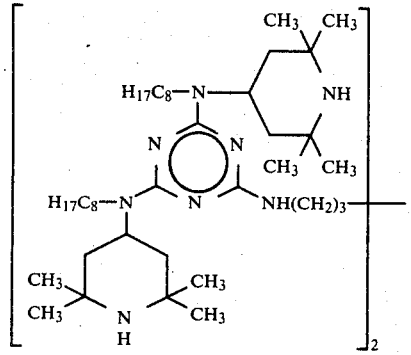

(f) Light stabilisers of the formula (VII)

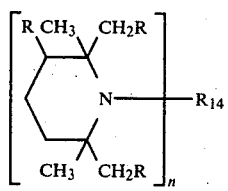

in which n is the number 1 or 2; R is as defined under the formula (I); and $R_{14}$ when n is 1 is $C_4$–$C_{18}$ alkyl, $C_7$–$C_{12}$ aralkyl, the group —CO—$R_{15}$, or $C_1$–$C_4$ alkyl which is substituted by —CN, —COOR$_{16}$, —OH, —OCOR$_{17}$ or

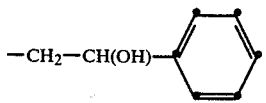

wherein $R_{15}$ is $C_1$–$C_{12}$ alkyl, $C_2$–$C_4$ alkenyl or phenyl, $R_{16}$ is $C_1$–$C_{18}$ alkyl, $R_{17}$ is $C_1$–$C_{18}$ alkyl, $C_2$–$C_{10}$ alkenyl, cyclohexyl, benzyl or $C_6$–$C_{10}$ aryl; or $R_{14}$ when n is 2 is $C_4$–$C_{12}$ alkylene, 2-butenylene-1,4, xylylene, the group —(C$_2$)$_2$—OOC—$R_{18}$—COO—(CH$_2$)$_2$— or the group —CH$_2$—OOC—$R_{19}$—COO—CH$_2$— wherein $R_{18}$ is $C_2$–$C_{10}$ alkylene, phenylene or cyclohexylene, and $R_{19}$ is $C_2$–$C_{10}$ alkylene, xylylene or cyclohexylene.

If any substituents are $C_1$–$C_{12}$ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl or n-dodecyl.

Any substituents which are $C_1$–$C_{18}$ alkyl can be for example the groups mentioned above, and in addition for example n-tridecyl, n-tetradecyl, n-hexadecyl or n-octadecyl.

If any groups are $C_2$–$C_{10}$ alkylene, these are in particular ethylene, propylene, 2,2-dimethylpropylene, tetramethylene, hexamethylene, octamethylene or decamethylene.

As $C_4$–$C_{18}$ alkyl, $R_{14}$ is for example n-butyl, sec-butyl, tert-butyl, n-hexyl, n-octyl, 2-ethyl-hexyl, 1,1-dimethyl-2-tert-butylethyl, n-nonyl, n-decyl, n-dodecyl, n-tridecyl, n-tetradecyl, n-hexadecyl or n-octadecyl.

If $R_{14}$ is a $C_1$–$C_4$ alkyl group substituted by —CN, it is for example cyanomethyl, cyanoethyl, 3-cyano-n-propyl or 4-cyano-n-butyl.

If $R_{14}$ is $C_4$–$C_{12}$ alkylene, it is for example 2,2-dimethylpropylene, tetramethylene, hexamethylene, octamethylene, decamethylene or dodecamethylene.

If $R_{14}$ is $C_7$–$C_{12}$ aralkyl, it is in particular phenethyl, p-methyl-benzyl or especially benzyl.

As $C_2$–$C_4$ alkenyl, $R_{15}$ is for example vinyl, 1-propenyl, allyl, methallyl or 2-butenyl.

As $C_2$–$C_{10}$ alkenyl, $R_{17}$ is for example the groups mentioned for $R_{15}$ as alkenyl, and in addition for example crotyl, 2-hexenyl, 2-octenyl or 2-decenyl.

If $R_{17}$ is $C_6$–$C_{10}$ aryl, it is for example phenyl which is unsubstituted or substituted in the o- or p-position by methyl, ethyl, isopropyl, n-butyl or tert-butyl.

The following compounds are examples of polyalkylpiperidine light stabilisers of this class:

(60) bis-[β-(2,2,6,6-tetramethylpiperidino)-ethyl]-sebacate,

(61) α-(2,2,6,6-tetramethylpiperidino)-acetic acid-n-octyl ester, and

(62) 1,4-bis-(2,2,6,6-tetramethylpiperidino)-2-butene.

(g) Light stabilisers of the formula (VIII)

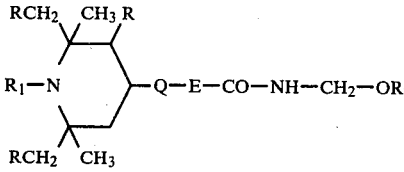

in which Q is —N(R$_3$)— or —O—; E is $C_1$–$C_3$ alkylene, the group —CH$_2$—CH(R$_4$)—O— wherein $R_4$ is hydrogen, methyl or phenyl, the group —(CH$_2$)$_3$—NH— or a single bond; R is hydrogen or methyl; $R_1$ is hydrogen, $C_1$–$C_{18}$ alkyl, $C_3$–$C_8$ alkenyl, $C_3$–$C_8$ alkynyl, $C_7$–$C_{12}$ aralkyl, $C_1$–$C_8$ alkanoyl, $C_3$–$C_5$ alkenoyl or glycidyl; $R_2$ is hydrogen or $C_1$–$C_{18}$ alkyl; $R_3$ is hydrogen, $C_1$–$C_{18}$ alkyl, $C_5$–$C_7$ cycloalkyl, $C_7$–$C_{12}$ aralkyl, cyanoethyl, $C_6$–$C_{10}$ aryl, the group —CH$_2$—CH(R$_4$)—OH wherein $R_4$ has the meaning defined above, a group of the formula

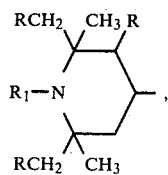

or a group of the formula

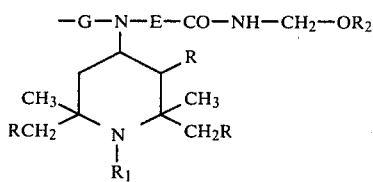

wherein G can be $C_2$–$C_6$ alkylene or $C_6$–$C_{12}$ arylene; or $R_3$ is a group —E—CO—NH—$CH_2$—$OR_2$.

If any substituents are $C_1$–$C_{18}$ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl, n-dodecyl, n-tridecyl, n-tetradecyl, n-hexadecyl or n-octadecyl.

If any substituents are $C_7$–$C_{12}$ aralkyl, they are for example phenethyl or in particular benzyl.

If $R_1$ is $C_3$–$C_8$ alkenyl, it can be for example 1-propenyl, allyl, methallyl, 2-butenyl, 2-pentenyl, 2-hexenyl, 2-octenyl or 4-tert-butyl-2-butenyl.

As $C_3$–$C_8$ alkynyl, $R_1$ is preferably propargyl. As $C_1$–$C_8$ alkanoyl, $R_1$ is for example formyl, propionyl, butyryl, octanoyl but preferably acetyl; and as $C_3$–$C_5$ alkenoyl, $R_1$ is especially acryloyl.

As $C_5$–$C_7$ cycloalkyl, $R_3$ is in particular cyclohexyl.

As $C_6$–$C_{10}$ aryl, $R_3$ is particularly phenyl, or α- or β-naphthyl which is unsubstituted or substituted with halogen or $C_1$–$C_4$ alkyl. As $C_1$–$C_3$ alkylene, E is for example methylene, ethylene or propylene.

As $C_2$–$C_6$ alkylene, G is for example ethylene, propylene, 2,2-dimethylpropylene, tetramethylene or hexamethylene; and as $C_6$–$C_{12}$ arylene, G is o-, m- or p-phenylene, 1,4-napthylene or 4,4'-diphenylene.

The following compounds are examples of polyalkylpiperidine light stabilisers of this class:

(63) N-hydroxymethyl-N'-2,2,6,6-tetramethylpiperidin-4-yl-urea,

(64) N-methoxymethyl-N'-2,2,6,6-tetramethylpiperidin-4-yl-urea,

(65) N-methoxymethyl-N'-n-dodecyl-N'-2,2,6,6-tetramethylpiperidin-4-yl-urea, and

(66) O-(2,2,6,6-tetramethylpiperidin-4-yl)-N-methoxymethyl-urethane.

(f) Polymeric compounds of which the recurring structural unit contains a polyalkylpiperidine radical of the formula (I), especially polyesters, polyethers, polyamides, polyamines, polyurethanes, polyureas, polyaminotriazines, poly(meth)acrylates or poly(meth)acrylamides, and copolymers thereof which contain such radicals.

The compounds of the following formulae, wherein m is a number from 2 to about 200 inclusive, are examples of polyalkylpiperidine light stabilisers of this class.

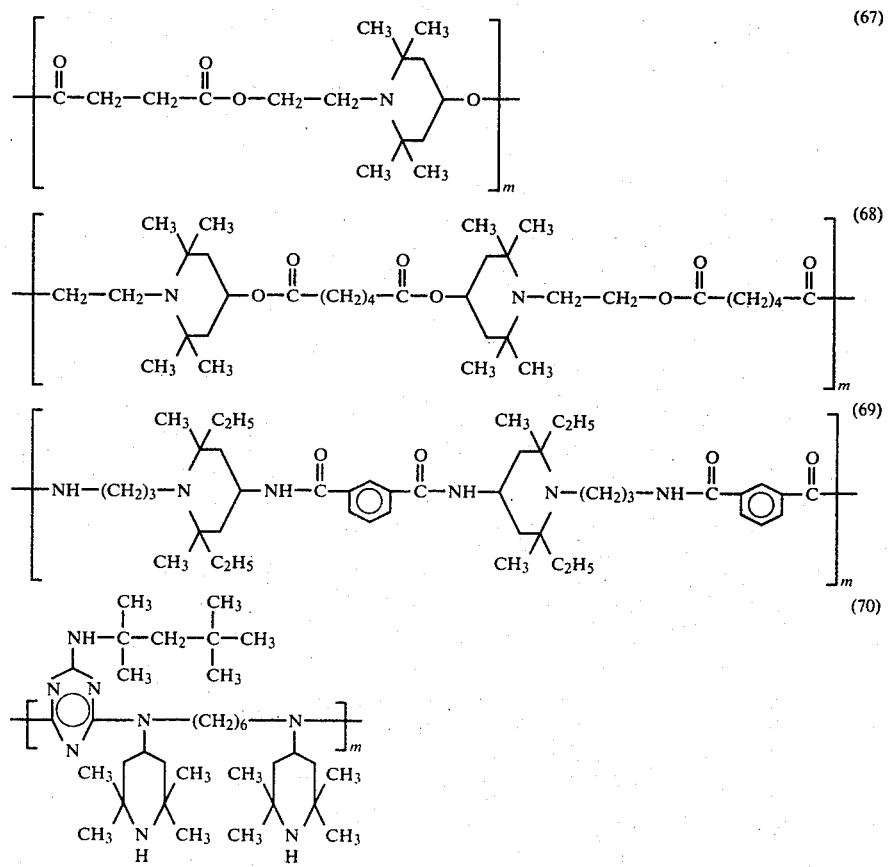

-continued

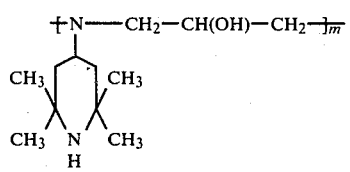 (71)

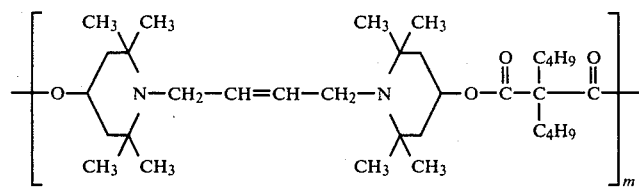 (72)

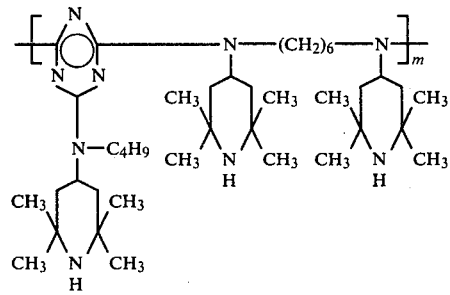 (73)

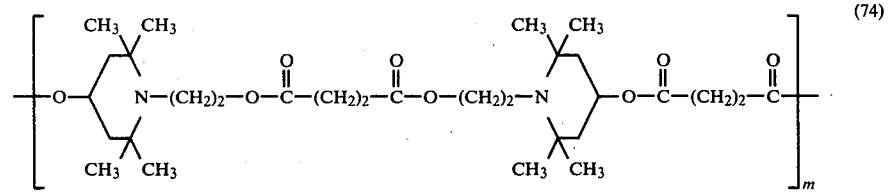 (74)

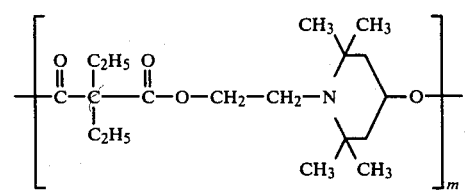 (75)

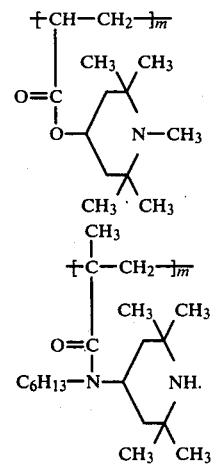 (76)

(77)

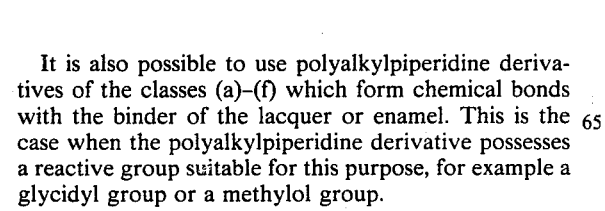

It is also possible to use polyalkylpiperidine derivatives of the classes (a)–(f) which form chemical bonds with the binder of the lacquer or enamel. This is the case when the polyalkylpiperidine derivative possesses a reactive group suitable for this purpose, for example a glycidyl group or a methylol group.

Examples of such compounds are the polyalkylpiperidine derivatives of the class (g) containing methylol or methylol ether groups.

Provided the polyalkylpiperidine derivatives are basic compounds, they can form salts with acids. Suitable acids are for example inorganic acids or organic carboxylic, sulfonic, phosphonic or phosphinic acids, such as hydrochloric acid, boric acid, phosphoric acid, acetic acid, salicylic acid, toluenesulfonic acid or benzenephosphonic acid.

The polyalkylpiperidine compounds can form complexes with complex-forming metal compounds, for example with zinc-II-acetate, cobalt-II-acetylacetonate, nickel-II-acetylacetonate, aluminum-III-acetylacetonate, nickel-II-benzoate or aluminum-III-benzoylacetonate.

The following examples are presented for the purpose of illustration only and are not to be construed to limit the nature of scope of the instant invention in any manner whatsoever.

EXAMPLE 1

2-Nitro-2'-hydroxy-3',5'-di-tert-octylazobenzene

To a 5-liter, 3-necked flask fitted with a stirrer and thermometer, was charged 317.3 grams of a 26% aqueous solution of technical naphthalenesulfonic acid, 6.7 grams of Triton X-207 (non-ionic surfactant), 19.6 grams of Conco AAS-90F (sodium dodecylbenzenesulfonate) and 315 ml of water. The mixture was warmed to 40° C. and then 393.6 grams of 2,4-di-tert-octylphenol was slowly added to the mixture with vigorous stirring keeping the temperature at 40° C.

A cold solution of o-nitroaniline diazonium chloride, prepared from 174.3 grams (1.26 mole) of o-nitroaniline and 87.1 grams (1.26 mole) of sodium nitrite in concentrated aqueous hydrochloric acid solution at a temperature of −5° to 0° C., was added dropwise into the reaction mixture over a 1.5-hour period. The resulting deep red to black reaction mixture was kept at 40° C. overnight. The temperature was raised to 65° C. for 1 hour; then the 95° C. for another 30 minutes. After cooling to 35° C., the reaction mixture was isolated as a fine dark red solid by filtration.

The crude product was triturated with 3.5 liters of water; then with 1400 ml of methanol and stirred in a blender, and filtered to yield a fine granular product. The dark red o-nitroazobenzene intermediate named above was obtained in a yield of 419.7 grams (72.7% of theory) and melted at 110°–112° C. Thin layer chromatography indicated a homogeneous product.

EXAMPLE 2

2-(2-Hydroxy-3,5-di-tert-octylphenyl)-2H-benzotriazole

To a 5-liter 3-necked flask fitted with a stirrer, thermometer, reflux condeser and nitrogen inlet was charged 400 grams (0.855 mol) of the o-nitroazobenzene intermediate of Example 1 and 1200 ml of toluene. To the resulting solution was added 260 ml of isopropanol and 260 ml of water. A nitrogen atmosphere was imposed and 175 ml of 50.1% aqueous sodium hydroxide was added. A flask containing 170.0 gram (2.6 gram-atoms) of zinc was connected to the reaction flask by Gooch rubber tubing and the zinc dust was added portionwise to the reaction mixture over a 120-minute period. The zinc was added at such a rate to keep the internal temperature at 70° C. After the zinc was all added, an additional 30 ml of 50.1% sodium hydroxide and 20 grams of zince were added to insure complete reaction. The reaction mixture was heated for 3 hours at 70° C. The mixture was cooled to room temperature by standing overnight and acidified with 500 ml of concentrated hydrochloric acid.

The zinc sludge was removed by filtration. The product was contained in the organic layer, which was washed with three 1000 ml portions of water, then 500 ml of saturated salt solution, and then dried over anhydrous sodium sulfate. The organic solvent was removed in vacuo to yield a crude product as a viscous syrup which crystallized on standing.

The crude product was recrystallized twice from 1000–1100 ml of ethanol to give 253 grams (67.8% of theory) of a pale yellow solid melting at 105°–106° C. of the above named compound. (Compound 1).

Analysis: Calcd for $C_{28}H_{41}N_3O$: C: 77.20; H,9.49; N:9.65. Found C: 77.22; H,9.14; N:9.77.

EXAMPLE 3

4-Chloro-2-nitro-2'-hydroxy-3',5'-di-tert-octylazobenzene

Coupling of 2,4-di-tert-octylphenyl with diazotized 4-chloro-2-nitroaniline using the procedure of Example 1 furnished the above-named compound as a deep red solid in 61.6% yield.

EXAMPLE 4

5-Chloro-2-(2-hydroxy-3,5-di-tert-octylphenyl)-2H-benzotriazole

When, using the general procedure of Example 2, the amount of 4-chloro-2-nitro-2'-hydroxy-3',5'-di-tert-octylazobenzene was substituted for 2-nitro-2'-hydroxy-3',5'-di-tert-octylazobenzene, the above-named compound was prepared in a yield of 71.8% as pale yellow crystals melting at 121°–122° C. (Compound 2)

Analysis: Calcd for $C_{28}H_{40}ClN_3O$: C: 71.54; H,8.58; N:8.94. Found C: 71.26; H,8.46; N:9.03.

EXAMPLE 5

Resistance to Loss of Benzotriazole Stabilizers

A number of 2-aryl-2H-benzotriazole light stabilizers were subjected to thermal gravimetric analysis both isothermally at 280° C. to indicate the time in minutes to reach 10%, 50% and 100% weight loss of the stabilizer as well as in a scanning mode at a heating rate of 10° (C. per minute to ascertain the temperature at which 10% and 50% weight loss of stabilizer were observed.

Experimental data are given on Table A.

These results correlate closely with the resistance of the indicated stabilizer to exudation or volatilization during any processing step with polymer formulations during the preparation of sheet, film, fiber or other fabricated pellicles. The absence or essential absence of exuded or volatilized stabilizer on processing equipment (i.e., rollers, guides, orifices, and the like) increases significantly the times between required shut-downs of continuously operated process equipment and represents enormous practical and economic savings related to the specific stabilizer used.

TABLE A

| | TGA Data | | | | |
|---|---|---|---|---|---|
| | Isothermal at 280° C. Time (minutes) to Indicated Weight Loss of Stabilizer | | | Scanning (at 10° C.) per minute Temperature °C. to Indicated Weight Loss of Stabilizer | |
| Stabilizer* | 10% | 50% | 100% | 10% | 50% |
| TINUVIN P | 0.4 | 0.75 | 1.2 | 182 | 215 |
| TINUVIN 350 | 0.6 | 1.0 | 1.8 | 210 | 247 |
| CYASORB UV-5411 | 0.6 | 1.9 | 3.5 | 225 | 260 |

TABLE A-continued

| | TGA Data | | | | |
|---|---|---|---|---|---|
| | Isothermal at 280° C. Time (minutes) to Indicated Weight Loss of Stabilizer | | | Scanning (at 10° C.) per minute Temperature °C. to Indicated Weight Loss of Stabilizer | |
| Stabilizer* | 10% | 50% | 100% | 10% | 50% |
| Compound 1 | 1.0 | 3.2 | 6.0 | 240 | 280 |

*TINUVIN P is 2-(2-hydroxy-5-methylphenyl)-2H-benzotriazole.
TINUVIN 350 is 2-(2-hydroxy-3-tert-butyl-5-sec-butylphenyl)-2H-benzotriazole.
CYASORB UV-5411 is 2-(2-hydroxy-5-tert-octylphenyl)-2H-benzotriazole.

Compound 1 (Example 2) clearly exhibits less volatility than the closest benzotriazole stabilizers. Compound 1 incorporated in a stabilized polymer composition would remain there during processing permitting excellent processability coupled with a final polymer pellicle with greater protection against subsequent light-induced deterioration.

EXAMPLE 6

Retention of Benzotriazole Stabilizers in Polycarbonate During Sheet Production

Polycarbonate (Lexan, General Electric) resin was formulated with 0.3% by weight of a number of 2-aryl-2H-benzotriazole light absorber stabilizers. The formulated resin was extruded at 600° F. (316° C.) into thin sheets. The resultant sheets were dissolved in methylene chloride and the polycarbonate precipitated with methanol. The amount of benzotriazole stabilizer retained in the polycarbonate sheet after fabrication was determined by gas chromatographic analysis.

The results are given on Table B.

TABLE B

| Stabilizer* | % Retained in Polycarbonate Sheet after Fabrication |
|---|---|
| TINUVIN 350 | 82 |
| CYASORB UV-5411 | 87 |
| Compound 1 | 100 |

*See Table A for chemical names of these stabilizers.

These data confirm the results on Table A that the instant Compound 1 resists loss by volatilization during processing.

EXAMPLE 7

Resistance to Loss During Cure and Weathering of Benzotriazole Stabilizers in Thermost Acrylic Coatings Several thermoset acrylic resin and an alkyd/acrylic resin systems were formulated with 2% by weight of several benzotriazole light absorber stabilizers and cast onto glass plates at 1μ thick coatings. The coatings were then cured by heating at elevated temperatures for selected periods of time. The loss of benzotriazole light stabilizer was then ascertained by UV-absorption analysis of the coatings. Any decrease in absorbance of the coatings can be correlated to loss of benzotriazole stabilizer during the curing step.

These cured coatings were also subjected to the accelerated (quick) weathering test (QUV) involving alternating 4-hour period of UV irradiation at 60° C. with a 4-hour period of condensation (rain) at 50° C. for each cycle for a total of 670 hours. Again any decrease in absorbance of the weathered coatings can be correlated to loss of the benzotriazole stabilizer during the curing and weathering period.

Results are given on Table C.

TABLE C

| | Absorbance Loss During Cure or Weathering (Percent) | | | | | |
|---|---|---|---|---|---|---|
| | Thermoset Acrylic Resin Systems | | | | | |
| | Single layer | | 2-Coat System | | High Solids | Alkyd/Acrylic Resin | |
| Stabilizer* | Heated 25 min at 120° C. | After Weathering | Heated 20 min at 135° C. | After Weathering | Heated 30 minutes at 150° C. | Heated 30 minutes at 125° C. | After Weathering |
| TINUVIN 328 | 25 | 35 | 59 | 69 | 95 | 77 | 100 |
| Compound 1 | 6 | 21 | 24 | 41 | 67 | 27 | 80 |

*TINUVIN 328 is 2-(2-hydroxy-3,5-di-tert-amyphenyl)-2H-benzotriazole.

As is seen from Table C, the instant compound exhibits far greater resistance to loss from the thermoset acrylic resin and alkyd/acrylic resin systems than did the close benzotriazole of the prior art. Compound 1 is discernibly less volatile than is TINUVIN 328 of closely related stucture.

EXAMPLE 8

Stabilization of Polyethylene Terephthalate 0.5% of the compound of Example 2 is added as a stabilizer to molten polyethylene terephthalate at 270° C. with stirring under a nitrogen atmosphere. The resulting formulated polymer is ground with solid carbon dioxide.

The stabilized composition is extruded at elevated temperature into a film with little loss of stabilizer. The film is then exposed to actinic radiation. The stabilized film retains desirable physical properties for a longer period than does a film prepared from unstabilized polyester.

EXAMPLE 9

Stabilization of Polycarbonate

Polycarbonate (Lexan, General Electric) is mixed in a compounding extruder with 0.3% of the compound of Example 4. The stabilized composition is extruded into a sheet at elevated temperature with little loss of stabilizer. The sheet maintains physical properties after exposure to UV light for a longer period than does a sheet containing no stabilizer.

The delamination of U.V. transparent automotive topcoats when applied over epoxy ester primer surfaces is a serious problem for automobile manufacturers. This problem is particularly exacerbated when the final coating film thickness is below specification. The incorporation of UV absorbers into the topcoats is indicated as a way to protect said topcoats from delamination and to prevent undue loss of gloss.

EXAMPLE 10

Gloss and Delamination Values of Topcoats of Thermoplastic Acrylic Lacquer

A silver metallic thermoplastic acrylic lacquer was formulated to include a benzotriazole light stabilizer and then was sprayed as a topcoat over a primer surface consisting of an epoxy ester on a metallic panel. The cure schedule was heating for 10 minutes at 48° C. and then for 30 minutes at 155° C. The initial topcoat film thickness was 2.0 to 2.2 mils (50 to 55 microns, 0.0508 to 0.0559 mm).

The panels were then exposed for one year in South Florida in an unheated black box at an angle of 5° to the sun.

The panels following the South Florida Black Box Exposure were contained for 96 hours in a constant humidty chamber at 38° C. and 100% relative humidity. The panels were then removed from the chamber, wiped dry and immediately evaluated using the cross-hatch tape adhesion test. The panels were then allowed to recover for one hour at room temperature before the cross-hatch tape adhesion test was run at a different spot on the same panel. Samples generally show some improved delamination resistance following the one hour recovery period from the most severe delamination condition namely immediately after humidification.

The cross-hatch tape adhesion test involves using a multi-cut knife to prepare cross-hatches through the topcoat film on the panel. A acetate fiber adhesive tape is placed over the cross-hatch area and then is pulled off. A visual inspection of the amount of topcoat, if any, coming off with the tape as it is pulled gives a relative rating of the amount of delamination. A rating system of 0 meaning no cross-hatch delamination to 5 meaning complete cross-hatch delamination is used.

Results are given on Tables D and E.

TABLE D

20° Gloss Values of Silver Metallic Thermoplastic Acrylic Lacquer*
After 5° South Florida Black Box Exposure

| Stabilizers** (% by wt.) | Initial | After 6 Months (Florida) | After 1 Year (Florida) | After 1 Year Polished*** |
|---|---|---|---|---|
| None | 77.8 | 15.1 | 1.6 | 4.4 |
| 1% Compound 1 | 77.7 | 38.0 | 2.6 | 7.7 |
| 2% TINUVIN 328 | 77.1 | 34.9 | 8.5 | 13.7 |
| 2% TINUVIN 350 | 77.5 | 37.5 | 6.0 | 24.3 |
| 2% Compound 1 | 77.5 | 35.4 | 7.1 | 14.7 |
| 2% Compound 2 | 78.3 | 36.7 | 3.5 | 9.4 |

*Thermoplastic acrylic lacquer is based on a binder of 60% poly(methyl methacrylate), 20% cellulose acetate butyrate and 20% plasticizer with about 3 phr of metallic pigment.
**See Tables A and C for chemical names of these stabilizers.
***One half of each panel was polished with DuPont #7 auto polish.

TABLE E

Delamination Values of Silver Metallic Thermoplastic Acrylic Lacquer*
After One Year 5° South Florida Black Box Exposure

| | Delamination Rating (0 to 5) | |
|---|---|---|
| Stabilizer** (% by wt.) | Immediately after Humidity Conditioning | After One Hour Recovery at Room Temperature After Humidity Conditioning |
| None | 5 | 5 |
| 1% Compound 1 | 5 | 3 |
| 2% TINUVIN 328 | 5 | 2 |
| 2% TINUVIN 350 | 3 | 2 |

TABLE E-continued

Delamination Values of Silver Metallic Thermoplastic Acrylic Lacquer*
After One Year 5° South Florida Black Box Exposure

| | Delamination Rating (0 to 5) | |
|---|---|---|
| Stabilizer** (% by wt.) | Immediately after Humidity Conditioning | After One Hour Recovery at Room Temperature After Humidity Conditioning |
| 2% Compound 1 | 5 | 3 |
| 2% Compound 2 | 3 | 1 |

*See description of lacquer on Table D
**See Tables A and C for chemical names of these stabilizers.

The data on Table D confirm that the instant compounds 1 and 2 exhibit resistance to loss during prolonged exposure in the South Florida Black Box test comparable to other benzotriazole light stabilizers.

The data on Table E show that the instant compounds, particularly compound 2, protect a thermoplastic acrylic topcoat from delamination after one year of South Florida Black Box Exposure under the most severe testing conditions immediately following humidification.

EXAMPLE 11

Delamination Values of Topcoats of Thermoset Acrylic Enamels

Two silver metallic thermoset acrylic enamels were formulated to include a benzotriazole light stabilizer and then sprayed as a topcoat over a primer surface consisting of an epoxy ester on a metal panel. The cure schedule was 17 minutes at 130° C. to give an initial topcoat film thickness of 1.7 mils (42 microns, 0.0432 mm). This panel was then exposed for 1200 hours in the QUV weathering test described in Example 7.

The panels following the QUV exposure were humidified, then tested for delamination resistance, then allowed to recover for one hour and then retested for delamination resistance as described in Example 10.

Results are given on Table F.

TABLE F

Delamination Values of Silver Metallic Thermoset Acrylic Enamel After 1200 Hours CUV Exposure

| | Delamination Rating (0 to 5) | | | |
|---|---|---|---|---|
| | Enamel* A | | Enamel* B | |
| Stabilizer (% by wt.) | Immediately After Humidity Conditioning | After One Hour Recovery at Room Temperature after Humidity Conditioning | Immediately After Humidity Conditioning | After One Hour Recovery at Room Temperature after Humidity Conditioning |
| None | 3 | 1 | 5 | 3 |
| 1% Compound 1 | 1 | 1 | 0 | 0 |
| 2% Compound 1 | 0 | 0 | 0-1 | 0 |

*Thermoset acrylic enamel is based on a binder of 70% of acrylic monomers such as hydroxyethyl acrylate, styrene, acrylonitrile, butyl acrylate and acrylic acid with 30% of a melamine resin. Enamel A is a lower 40-45% solids solution while Enamel B is a non-aqueous dispersion (NAD) having about 45-50% solids with about 3 phr of metallic pigment.

The combination of hindered amine light stabilizers and the instant benzotriazole UV light absorbers provides a particularly beneficial solution to the combined goal of gloss retention and delamination resistance in metallic thermoset acrylic enamels and in metallic thermoplastic acrylic lacquers for automotive topcoats.

The hindered amine light stabilizers even at low concentrations (0.5% by weight) protect the thermoset acrylic enamels and thermoplastic acrylic lacquers against loss of gloss, but do not act as UV light screens. Accordingly, UV light can pass through the acrylic topcoat in the absence of a UV light absorber, such as the instant benzotriazoles, and cause deterioration and failure in epoxy ester primer surface beneath the topcoat. Incorporation of even low concentrations (0.5% by weight) of a benzotriazole in combination with a hindered amine provides both gloss retention and resistance to delamination for the metallic acrylic topcoats.

EXAMPLE 12

Delamination Values of Topcoats of Thermoset Acrylic Enamels

Two silver metallic thermoset acrylic enamels are formulated to include both a hindered amine light stabilizer and a benzotriazole light absorber. Test panels are prepared and tested as described in Example 11.

When the thermoset acrylic enamel described in Table F contains a hindered amine light stabilizer such as bis-(2,2,6,6-tetramethyl-4-piperidyl) sebacate or bis-(1,2,2,6,6-pentamethyl-4-piperidyl) 2-n-butyl-2-(3,5-di-tert-butyl-4-hydroxybenzyl) malonate alone delamination rating values are esentially the same as those for the unstabilized enamel. Excellent delamination rating values are obtained when a combination of the hindered amine light stabilizer and the instant benzotriazole UV absorbers are used to stabilize the enamel.

EXAMPLE 13

Delamination and 20° Gloss Values of Thermoplastic Acrylic Lacquers

The efficacy of combinations of hindered amine light stabilizers and the instant benzotriazole light absorbers in providing highly beneficial protection to automotive topcoats is well demonstrated with thermoplastic acrylic resins wherein both gloss retention after prolonged exposure in South Florida is provided by the hindered amine component while the instant benzotriazole light absorber protects the thermoplastic acrylic topcoat from delamination.

A silver metallic thermoplastic acrylic lacquer is formulated to include both a hindered amine light stabilizer and a benzotriazole light absorber. Test panels are prepared and tested as described in Example 10.

The lacquer containing both a hindered amine light stabilizer (such as those named in Example 12) and a benzotriazole UV absorber (such as Compound 1 or 2) exhibited excellent 20° Gloss Values and Delamination Values.

EXAMPLE 14

The combination of certain benzotriazole UV absorbers with the normal barium/cadmium poly (vinyl chloride) PVC thermal stabilizers leads to discoloration thus limiting the usefulness of said benzotriazoles in certain PVC applications where discoloration is counterindicated.

The instant benzotriazole (Compound 1) was much more resistant to discoloration in the presence of such PVC thermal stabilizers than were the prior art benzotriazoles such as 2-(2-hydroxy-5-methylphenyl)-2H-benzotriazole and the like.

What is claimed is:

1. An automotive topcoat finish, lacquer or enamel composition exhibiting retention of gloss and resistance to delamination on weathering which comprises
   (a) a thermoplastic acrylic resin or a thermoset acrylic resin,
   (b) 0.1 to 5% by weight of resin of a compound of the formula

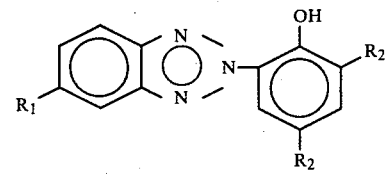

wherein
$R_1$ is hydrogen or chloro, and
$R_2$ is tert-octyl, and
   (c) 0.1 to 5% by weight of resin of a hindered amine light stabilizer.

2. A composition according to claim 1 containing 0.5 to 2% by weight of component (b) based on resin, and 0.5 to 2% by weight of component (c) based on resin.

3. A composition according to claim 1 wherein component (b) is 2-(2-hydroxy-3,5-di-tert-octyl-phenyl)-2H-benzotriazole.

4. A composition according to claim 1 wherein component (c) is a light stabilizer of the formula (II)

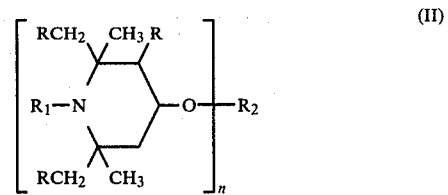

in which n is a number from 1-4 inclusive; R is hydrogen or methyl; $R_1$ is hydrogen, oxyl, $C_1$-$C_{18}$ alkyl, $C_3$-$C_8$ alkenyl, $C_1$-$C_8$ alkynyl, $C_7$-$C_{12}$ aralkyl, $C_1$-$C_8$ alkanoyl, $C_3$-$C_5$ alkenoyl, glycidyl or a group —CH$_2$—CH(OH)—Z wherein Z is hydrogen, methyl or phenyl; and $R_2$ when n is 1 is hydrogen, $C_1$-$C_{18}$ alkyl optionally interrupted by one or more oxygen atoms, cyanoethyl, benzyl, glycidyl, a monovalent radical of an aliphatic, cycloaliphatic, araliphatic or aromatic carboxylic acid, or of carbamic acid or of a phosphorus-containing acid, or a monovalent silyl radical; $R_2$ when n is 2 is $C_2$-$C_{12}$ alkylene, $C_4$-$C_{12}$ alkenylene, xylylene, a bivalent radical of an aliphatic, cycloaliphatic, araliphatic or aromatic dicarboxylic acid, of dicarbamic acid or of a phosphorus-containing acid, or a bivalent silyl radical; $R_2$ when n is 3 is a trivalent radical of an aliphatic, cycloaliphatic or aromatic tricarboxylic acid, of an aromatic tricarbamic acid or of a phosphorus-containing acid, or a trivalent silyl radical; and $R_2$ when n is 4 is a tetravalent radical of an aliphatic, cycloaliphatic or aromatic tetracarboxylic acid.

5. A composition according to claim 4 where in the light stabilizer of Formula II n is the number 1 or 2; R is hydrogen or methyl; $R_1$ is hydrogen, $C_1$-$C_{12}$ alkyl, allyl, benzyl, acetyl or acryloyl; and $R_2$ when n is 1 is a radical of an aliphatic carboxylic acid having 2-18 C atoms, of a cycloaliphatic carboxylic acid having 5-12 C atoms or of an aromatic carboxylic acid having 7-15

C atoms; and $R_2$ when n is 2 is a radical of an aliphatic dicarboxylic acid having 2–36 C atoms, of a cycloaliphatic or aromatic dicarboxylic acid having 8–14 C atoms, or of an aliphatic, cycloaliphatic or aromatic dicarbamic acid having 8–14 C atoms.

6. A composition according to claim 1 wherein compound (c) is a light stabiliser of the formula (III)

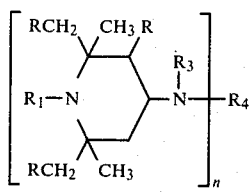
(III)

in which n is the number 1 or 2; R is hydrogen or methyl; $R_1$ is hydrogen, oxyl, $C_1$–$C_{18}$ alkyl, $C_3$–$C_8$ alkenyl, $C_3$–$C_8$ alkynyl, $C_7$–$C_{12}$ aralkyl, $C_1$–$C_8$ alkanoyl or $C_3$–$C_5$ alkenoyl; $R_3$ is hydrogen, $C_1$–$C_{12}$ alkyl, $C_5$–$C_7$ cycloalkyl, $C_7$–$C_8$ aralkyl, $C_2$–$C_{18}$ alkanoyl, $C_3$–$C_5$ alkenoyl or benzoyl; and $R_4$ when n is 1 is hydrogen, $C_1$–$C_{18}$ alkyl, $C_5$–$C_7$ cycloalkyl, $C_2$–$C_8$ alkenyl which is unsubstituted or substituted by a cyano, carbonyl or carbamide group, or it is glycidyl, a group of the formula —$CH_2$—CH(OH)—Z or of the formula —CONH—Z wherein Z is hydrogen, methyl or phenyl; or $R_4$ when n is 2 is $C_2$–$C_{12}$ alkylene, $C_6$–$C_{12}$ arylene, xylilene, a —$CH_2$—CH(OH)—$CH_2$— group or a group —$CH_2$—CH(OH)—$CH_2$—O—X—O—$CH_2$—CH(OH)—$CH_2$— wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a bivalent radical of an aliphatic, cycloaliphatic or aromatic dicarboxylic acid or dicarbamic acid, or can also be the group —CO—; or $R_3$ and $R_4$ together when n is 1 can be the cyclic radical of an aliphatic or aromatic 1,2- or 1,3-dicarboxylic acid.

7. A composition according to claim 1 wherein component (c) is a light stabiliser of the formula (IV)

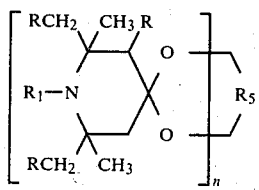
(IV)

in which n is the number 1 or 2; R is hydrogen or methyl; $R_1$ is hydrogen, oxyl, $C_1$–$C_{18}$ alkyl, $C_3$–$C_8$ alkenyl, $C_3$–$C_8$ alkynyl, $C_7$–$C_{12}$ aralkyl, $C_1$–$C_8$ alkanoyl or $C_3$–$C_5$ alkenoyl; and $R_5$ when n is 1 is $C_2$–$C_8$ alkylene or hydroxyalkylene or $C_4$–$C_{22}$ acyloxyalkylene; and $R_5$ when n is 2 is the group (—$CH_2$)$_2$C(—$CH_2$—)$_2$.

8. A composition according to claim 1 wherein component (c) is a light stabiliser of the formula (V)

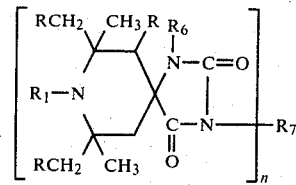
(V)

in which n is the number 1 or 2; R is hydrogen or methyl; $R_1$ is hydrogen, oxyl, $C_1$–$C_{18}$ alkyl, $C_3$–$C_8$ alkenyl, $C_3$–$C_8$ alkynyl, $C_7$–$C_{12}$ aralkyl, $C_1$–$C_8$ alkanoyl or $C_3$–$C_5$ alkenoyl; $R_6$ is hydrogen, $C_1$–$C_{12}$ alkyl, allyl, benzyl, glycidyl or $C_2$–$C_6$ alkoxyalkyl; and $R_7$ when n is 1 is hydrogen, $C_1$–$C_{12}$ alkyl, $C_3$–$C_5$ alkenyl, $C_7$–$C_9$ aralkyl, $C_5$–$C_7$ cycloalkyl, $C_2$–$C_4$ hydroxyalkyl, $C_2$–$C_6$ alkoxyalkyl, $C_6$–$C_{10}$ aryl, glycidyl, a group of the formula —($CH_2$)$_m$—COO—Q or of the formula —($CH_2$)$_m$—O—CO—Q wherein m is 1 or 2, and Q is $C_1$–$C_4$ alkyl or phenyl; or $R_7$ when n is 2 is $C_2$–$C_{12}$ alkylene or $C_6$–$C_{12}$ arylene, a group —$CH_2$—CH(OH)—$CH_2$—O—X—O—$CH_2$—CH(OH)—$CH_2$— wherein X is $C_2$–$C_{10}$ alkylene, $C_6$–$C_{15}$ arylene or $C_6$–$C_{12}$ cycloalkylene, or a group —$CH_2$CH(OZ')$CH_2$—(O$CH_2$—CH(OZ')$CH_2$)$_2$— wherein Z' is hydrogen, $C_1$–$C_{18}$ alkyl, allyl, benzyl, $C_2$–$C_{12}$ alkanoyl or benzoyl.

9. A composition according to claim 1 wherein component (c) is a light stabiliser of the formula (VI)

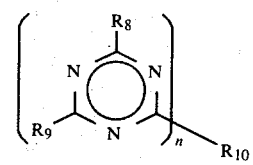
(VI)

in which n is the number 1 or 2; and $R_8$ is a group of the formula

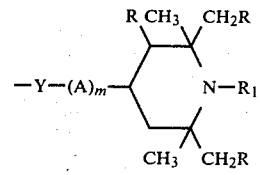

in which R is as defined under the formula (I), $R_1$ is as defined under (a), Y is —O— or —$NR_{11}$—, A is $C_2$–$C_6$ alkylene; and m is the number 0 or 1; $R_9$ is the groups $R_8$, $NR_{11}R_{12}$, —$OR_{13}$, —$NHCH_2OR_{13}$ or —N($CH_2OR_{13}$)$_2$; $R_{10}$ when n is 1 is the groups $R_8$ or $R_9$; and $R_{10}$ when n is 2 is the group —Y—Q—Y— wherein Q is $C_2$–$CH_6$ alkylene optionally interrupted by —N($R_{14}$)—; $R_{11}$ is $C_1$–$C_{12}$ alkyl, cyclohexyl, benzyl or $C_1$–$C_4$ hydroxyalkyl, or a group of the formula

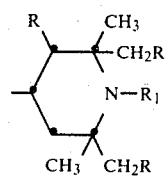

$R_{12}$ is $C_1$-$C_{12}$ alkyl, cyclohexyl, benzyl, $C_1$-$C_4$ hydroxyalkyl; $R_{13}$ is hydrogen, $C_1$-$C_{12}$ alkyl or phenyl; and $R_{14}$ is hydrogen or the group —$CH_2OR_{13}$; or $R_{11}$ and $R_{12}$ together are $C_4$-$C_5$ alkylene or oxaalkylene, or $R_{11}$ and $R_{12}$ are each a group of the formula

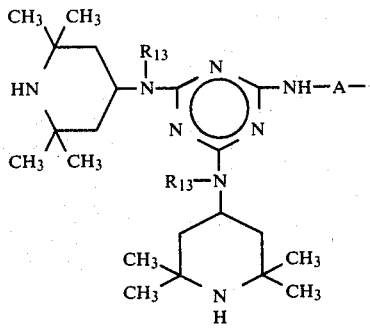

10. A composition according to claim 1 wherein component (c) is a light stabiliser of the formula (VII)

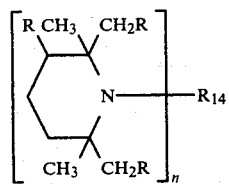
(VII)

in which n is the number 1 or 2; R is hydrogen or methyl; and $R_{14}$ when n is 1 is $C_4$-$C_{18}$ alkyl, $C_7$-$C_{12}$ aralkyl, the group —CO—$R_{15}$, or $C_1$-$C_4$ alkyl which is substituted by —CN, —COOR$_{16}$, —OH, —OCOR$_{17}$ or

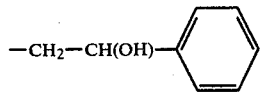

wherein $R_{15}$ is $C_1$-$C_{12}$ alkyl, $C_2$-$C_4$ alkenyl or phenyl, $R_{16}$ is $C_1$-$C_{18}$ alkyl, $R_{17}$ is $C_1$-$C_{18}$ alkyl, $C_2$-$C_{10}$ alkenyl, cyclohexyl, benzyl or $C_6$-$C_{10}$ aryl; or $R_{14}$ when n is 2 is $C_4$-$C_{12}$ alkylene, 2-butenylene-1,4, xylylene, the group —(CH$_2$)$_2$—OOC—R$_{18}$—COO—(CH$_2$)$_2$— or the group —CH$_2$OOC—R$_{19}$—COO—OH$_2$— wherein $R_{18}$ is $C_2$-$C_{10}$ alkylene, phenylene or cyclohexylene, and $R_{19}$ is $C_2$-$C_{10}$ alkylene, xylylene or cyclohexylene.

11. A composition according to claim 1 wherein component (c) is a light stabiliser of the formula (VIII)

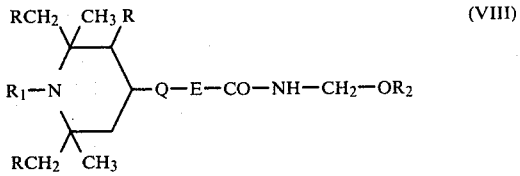
(VIII)

in which Q is —N(R$_3$)— or —O—; E is $C_1$-$C_3$ alkylene, the group —CH$_2$—CH(R$_4$)—O— wherein R$_4$ is hydrogen, methyl or phenyl, the group —(CH$_2$)$_3$—NH— or a single bond; R is hydrogen or methyl; $R_1$ is hydrogen, $C_1$-$C_{18}$ alkyl, $C_3$-$C_8$ alkenyl, $C_3$-$C_8$ alkynyl, $C_7$-$C_{12}$ aralkyl, $C_1$-$C_8$ alkanoyl, $C_3$-$C_5$ alkenoyl or glycidyl; $R_2$ is hydrogen or $C_1$-$C_{18}$ alkyl; $R_3$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —CH$_2$—CH(R$_4$)—OH wherein $R_4$ has the meaning defined above, a group of the formula

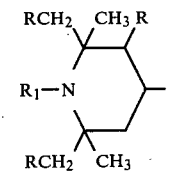

or a group of the formula

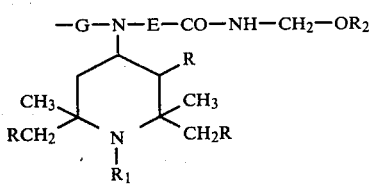

wherein G can be $C_2$-$C_6$ alkylene or $C_6$-$C_{12}$ arylene; or $R_3$ is a group —E—CO—NH—CH$_2$—OR$_2$.

12. A composition according to claim 1 wherein component (c) is bis-(2,2,6,6-tetramethyl-4-piperidyl) sebacate.

13. A composition according to claim 1 wherein component (c) is bis(1,2,2,6,6-pentamethyl-4-piperidyl) 2-n-butyl-2-(3,5-di-tert-butyl-4-hydroxybenzyl)malonate.

* * * * *

UNITED STATES PATENT AND TRADEMARK OFFICE
CERTIFICATE OF CORRECTION

PATENT NO. : 4,278,590
DATED : JULY 14, 1981
INVENTOR(S) : MARTIN DEXTER AND ROLAND A. E. WINTER

It is certified that error appears in the above—identified patent and that said Letters Patent is hereby corrected as shown below:

Claim 9, Column 36, Line 57 reads:

"is $C_2$-$CH_6$ alkylene optionally interrupted by $-N(R_1-$"

Should read:

"is $C_2$-$C_6$ alkylene optionally interrupted by $-N(R_1-$"

Signed and Sealed this

Twentieth Day of October 1981

[SEAL]

Attest:

GERALD J. MOSSINGHOFF

Attesting Officer

Commissioner of Patents and Trademarks